(12) United States Patent
Rasche

(10) Patent No.: US 6,473,635 B1
(45) Date of Patent: Oct. 29, 2002

(54) METHOD OF AND DEVICE FOR DETERMINING THE POSITION OF A MEDICAL INSTRUMENT

(75) Inventor: Volker Rasche, Hamburg (DE)

(73) Assignee: Koninkiljke Phillip Electronics N.V., Eindhoven (NL)

( * ) Notice: Subject to any disclaimer, the term of this patent is extended or adjusted under 35 U.S.C. 154(b) by 21 days.

(21) Appl. No.: 09/675,244

(22) Filed: Sep. 29, 2000

(30) Foreign Application Priority Data

Sep. 30, 1999 (DE) .......................................... 199 46 948

(51) Int. Cl.⁷ ................................................ A61B 5/05
(52) U.S. Cl. ........................................ 600/428; 600/424
(58) Field of Search ................................. 600/424, 421, 600/422, 428, 431, 433, 435, 425, 436, 407, 437; 607/122; 324/307, 309; 378/8

(56) References Cited

U.S. PATENT DOCUMENTS

| | | | |
|---|---|---|---|
| 4,182,311 A | * 1/1980 | Seppi et al. | 250/363.02 |
| 4,547,892 A | * 10/1985 | Richey et al. | 378/8 |
| 5,730,129 A | 3/1998 | Darrow et al. | 128/653.1 |
| 5,840,025 A | * 11/1998 | Ben-Haim | 600/424 |
| 6,211,666 B1 | * 4/2001 | Acker | 128/899 |
| 6,216,027 B1 | * 4/2001 | Willis et al. | 600/424 |
| 6,233,478 B1 | * 5/2001 | Liu | 378/8 |
| 6,246,898 B1 | * 6/2001 | Vesely et al. | 600/424 |

* cited by examiner

*Primary Examiner*—Marvin M. Lateef
*Assistant Examiner*—Eleni Mantis Mercader
(74) *Attorney, Agent, or Firm*—John Vodopia

(57) ABSTRACT

The invention relates to a method of and a device for determining the position of a medical instrument (4), introduced into the body of a patient (2), relative to a periodically moving organ (3) of the body, which method includes the steps of:

a) determining the spatial position (c, r) of the medical instrument (4) and of a reference probe (6) while acquiring at the same time a periodic motion signal ($E_2$) which relates to the periodic motion of the body organ (3), b) selecting a 3D image data set (p) from an image data base which contains 3D image data sets (p) of the body organ (3) which have been acquired pre-operatively and simultaneously with the same motion signal ($E_1$) and are associated with individual motion phases ($e_1$, $e_2$, . . . ), in such a manner that that 3D image data set (p) is selected which is associated with the motion phase ($e_1$, $e_2$, . . . ) during the determination of the spatial position (c, r) of the medical instrument (4) and of the reference probe (6), and c) determining the position of the medical instrument (4) relative to the body organ (3) by converting the spatial position (6) of the medical instrument (4) by means of the positions of the reference probe which are known in space and in the selected 3D image data set.

14 Claims, 6 Drawing Sheets

METHOD OF AND DEVICE FOR DETERMINING THE POSITION OF A MEDICAL INSTRUMENT

BACKGROUND OF THE INVENTION

The invention relates to a method of and a device for determining the position of a medical instrument, introduced into the body of a patient, relative to a periodically moving organ of the body.

SUMMARY OF THE INVENTION

Clinical applications impose increasingly more severe requirements on the precision of the determination of the position of a medical instrument introduced into the body of a patient. Notably the growing interest in minimal-invasive methods for the treatment of cardiac diseases necessitates the development of methods and devices allowing the physician to guide a medical instrument to an accurately predetermined position inside or outside the heart. For example, in the case of direct myocardial revascularization it is necessary to guide a catheter with a small drill head to a plurality of predetermined positions on the ventricle wall in order to drill small holes therein or to administer a medicine directly to the ventricle wall in such positions.

According to a method which is known from Gepstein et al. "A Novel Method for Non-Fluoroscopic Catheter-Based Electroanatomical Mapping of the Heart", Circulation 1997; 95:1611–1622, the position of a catheter introduced into the body is measured in that on the catheter there is mounted an electromagnetic transmission device, for example, an RF coil, whereas a corresponding electromagnetic receiving device, for example a plurality of RF receiving coils, is arranged outside the body in order to receive the signals transmitted by the transmission device. Even though the position of the catheter, or the tip of the catheter, relative to the coordinate system of the receiving device, i.e. the position of the catheter in space, can thus be comparatively accurately determined, the position of the catheter relative to the surrounding anatomy, for example relative to the heart, cannot be determined in this manner. To this end, additionally X-ray fluoroscopy images would have to be formed during the treatment; such images would enable tracking of the catheter in continuously formed new X-ray images. Such fluoroscopic methods, however, are comparatively intricate on the one hand and do not provide the accuracy required for the determination of the position of the medical instrument. On the other hand, the continuous formation of X-ray images during the treatment of the patient represents an additional X-ray load. There is another problem in that the anatomy surrounding the medical instrument is not stationary during the treatment but moves, notably with a periodic motion. This holds above all for the heart which performs a periodic eigenmotion, i.e. which contracts during the systole and expands during the diastole and is also subject to an additional, practically periodic motion which is due to the respiration of the patient. Be it partly to a lesser extent, this holds not only for the heart, but also for other organs such as the brain, the stomach and the liver which are also moved by the cardiac and respiratory motions.

Therefore, it is an object of the invention to provide a method and a device which enable as accurate as possible determination of the position, relative to a periodically moving body organ, of a medical instrument introduced into the body of a patient.

This object is achieved by means of a method as disclosed in claim 1 and a device as disclosed in claim 10.

The invention is based on the recognition of the fact that the periodic motion of the body organ with respect to which the position of the medical instrument is to be determined can also be taken into account for the position determination. To this end, a periodic motion signal which is associated with the periodic motion of the body organ is measured, for example a respiratory motion signal which is dependent on the respiration of the patient or an electrocardiogram which is associated with the cardiac motion, while the spatial position of the medical instrument and of a reference probe is determined by means of a measuring device, for example by means of the known electromagnetic measuring device. The reference probe is then arranged outside the body of the patient, for example on the surface thereof or on the patient table, and is constructed in such a manner that its position can be determined by means of the position measuring unit. Alternatively, two reference probes may be provided, one reference probe being arranged on the body of the patient whereas the other is mounted on the patient table.

Before the medical intervention an image data acquisition unit, for example a magnetic resonance tomography unit, a computed tomography apparatus, an ultrasound device or an X-ray device has already formed an image data base in which there are taken up the individual 3D image data sets which have been acquired simultaneously with the periodic motion signal which is the same as that acquired during the intra-operative determination of the spatial positions, with each individual 3D image data set there being associated an individual motion phase within a period of the motion signal. Moreover, the reference probe must already be pre-operatively located at its ultimate point of application and its position relative to the 3D image data sets must be determined. This can be realized, for example, by constructing the reference probe in such a manner that it is also detected during the image data acquisition and that is recognizable in the individual 3D image data sets. Another possibility consists in determining the position of the reference probe relative to the image data acquisition unit, for example, by determining the position of the image data acquisition unit and the reference probe by means of the known position measuring unit.

On the basis of the motion phase during the determination of the spatial position of the medical instrument and the reference probe that 3D image data set which is associated with the same motion phase is then (intra-operatively) selected from the image data bank. The motion signal, or more exactly speaking the individual motion phase, thus quasi represents the link between the intra-operatively determined spatial position of the medical instrument and the pre-operatively determined 3D image data set which contains the information concerning the position of the anatomy in the same motion phase. Because the position of the reference probe relative to the body organ is also known in this 3D image data set and the actual spatial position of the reference probe was measured, a conversion formule can be determined therefrom; the measured spatial position of the medical instrument can thus be simply converted, for example by means of a simple co-ordinate transformation, into its position relative to the body organ. The invention thus enables exact determination of the position of a medical instrument, introduced into the body of a patient, relative to a periodically moving body organ, for example the position of a catheter introduced into a ventricle, and also the tracking of motions of the instruments. The physician can thus guide the instrument to accurately predetermined positions in which the desired interventions can be carried out.

Attractive versions and embodiments of the method according to the invention and the device according to the invention are disclosed in the further claims.

The decision as to which motion signal is recorded and used during the method according to the invention is dependent notably on the motion whereto the medical instrument introduced into the body is subject itself, or on the motion performed by the body organ in which or in the vicinity of which the medical instrument is to operate. In the case of a heart catheter this will notably be the cardiac motion, so that it is advantageous to record an electrocardiogram of the patient as the motion signal. In the case of interventions in the brain, an electrocardiogram is again suitable. In an advantageous embodiment a respiratory motion signal which is dependent on the respiratory motion of the patient is acquired as the motion signal.

In a further preferred embodiment such a respiratory motion signal is acquired in addition to another motion signal, for example the electrocardiogram, in order to be used during the determination of the position of the medical instrument in conformity with the described method so as to take into account and correct the motions of the anatomy, and possibly of the medical instrument, which are due to the respiration. This embodiment yields an even more accurate determination of position.

In a preferred embodiment, moreover, a 3D image data set is also acquired during the determination of the spatial position of the medical instrument and the reference probe; this can be realized by means of a real-time 3D ultrasound method and such a data set can be used during the determination of the position of the medical instrument relative to the body organ and/or can be taken up in the image data base. If desired, the accuracy of the position determination can thus be further enhanced. Moreover, information is thus made available concerning a real-time 3D image data set which can also be used for the formation of an image of the surroundings of the medical instrument from the selected 3D image data set, which image can then be displayed on a display device; the position of the medical instrument can be superposed on said image as is performed in a further preferred embodiment.

BRIEF DESCRIPTION OF THE DRAWINGS

The invention will be described in detail hereinafter with reference to the drawings. Therein.

DESCRIPTION OF THE PREFERRED EMBODIMENTS

Figure 1:
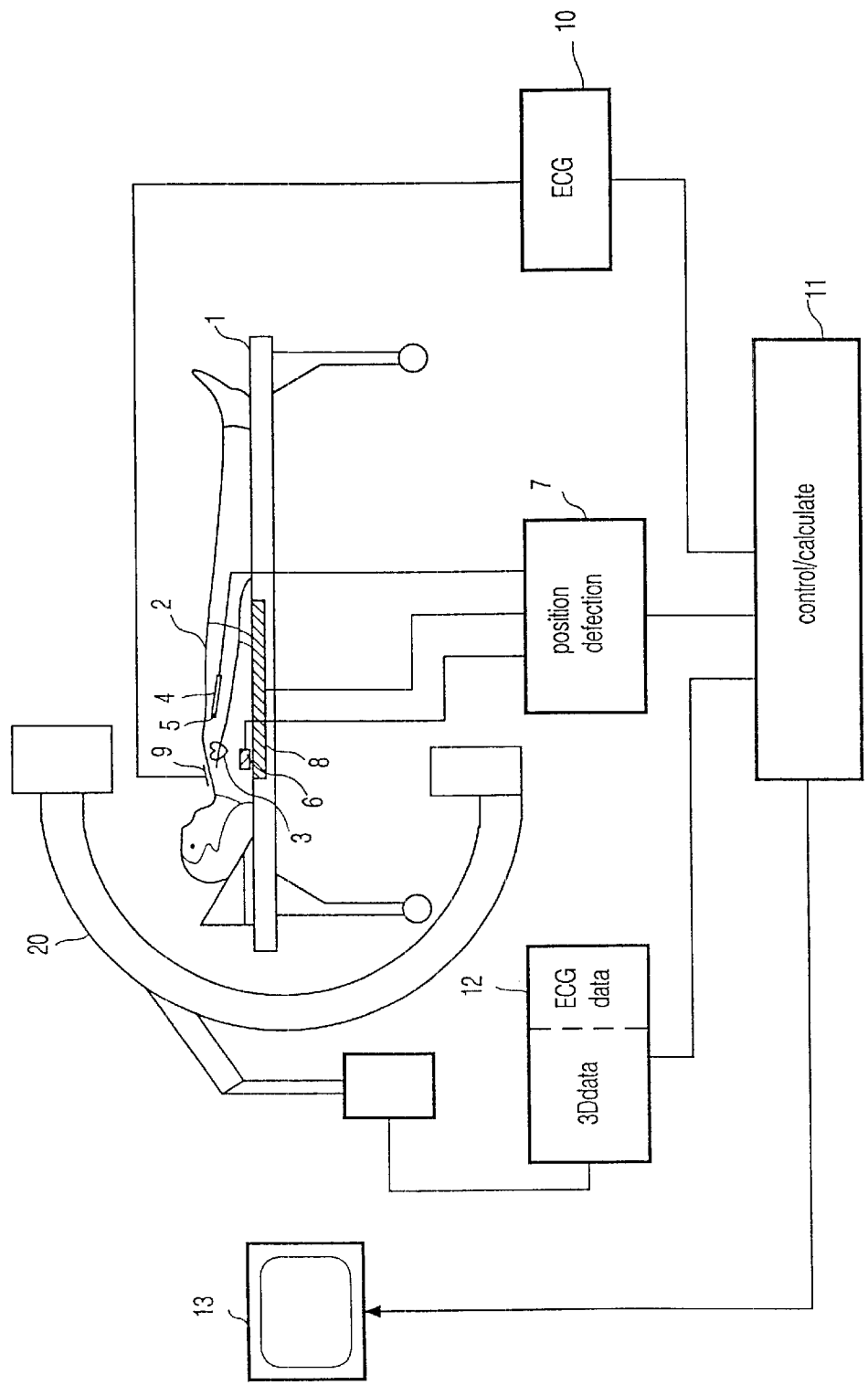
FIG. 1 shows a block diagram illustrating the method according to the invention.

The block diagram of FIG. 1 shows a patient 2 who is arranged on a patient table 1 and whose symbolically indicated heart 3 is to be subjected to a treatment by means of a catheter 4 introduced into the body. In addition to the treatment instrument (not shown), for example, a small laser or drill, an RF coil (5) for the transmission of RF signals is provided at the tip of the catheter. Underneath the patient 2 there is provided, for example integrated in the patient table 1, an RF receiving unit 8 for the reception of the signals transmitted by the RF coil 5; the unit 8 consists, for example, of an array with at least three adjacently arranged RF receiving coils. The catheter 4 with the RF transmitter coil 5 and the RF receiving unit 8 are connected to an RF processing unit 7 which constitutes a position measuring unit in conjunction with the RF transmitter coil 5 and the RF receiving unit 8. The RF processing unit 7 on the one hand controls the transmission of the RF signals by the coil 5 and on the other hand evaluates the signals received by the RF receiving unit 8 in order to calculate therefrom the position of the catheter 4 in a fixed system of co-ordinates, for example, in the system of co-ordinates of the RF receiving unit 8; the position in space of the catheter 4 is then determined therefrom.

Furthermore, a reference probe 6 which also includes RF transmission means, for example an RF transmitter coil, for transmitting RF signals is also connected to the RF processing unit 7; these signals can again be received by the RF receiving unit 8 and the position in space of the reference probe 6 can be determined therefrom. In the illustrated case the reference probe 6 is fixed to the patient table 1, but it may also be attached to the body surface of the patient 2, provided that the patient does not move during the treatment.

At the area of the chest of the patient 2 there is provided an electrode array 9 which is connected to an electrocardiography unit 10 so as to measure an electrocardiogram of the patient 2 during the treatment.

The RF processing unit 7 and the electrocardiography unit 10 are connected to a control and arithmetic unit 11 which controls said units and processes the data delivered thereby. Also connected to the control and arithmetic unit 11 is a storage unit 12 in which pre-operatively acquired 3D image data sets of the patient 2 are stored, that is, in this case image data of the cardiac region of the patient. Depending on the desired information and on the relevant application, such 3D image data sets may have been supplied by one or more medical imaging devices (image data acquisition unit 20) such as an X-ray device or a magnetic resonance tomography device. For such 3D image data sets to be suitable for the proposed method, however, it is necessary that the reference probe 6 was already present in its present location during the acquisition of the 3D image data sets and that its position relative to the image data acquisition unit 20 is known. It is also necessary that an electrocardiogram of the patient was acquired simultaneously with the acquisition of the 3D image data sets, so that each 3D image data set can be associated with a concrete cardiac motion phase, that is, with a given instant within the period of the electrocardiogram. The storage unit 12 thus contains a four-dimensional data set, that is, one or more 3D image data sets for each cardiac motion phase within the period of the electrocardiogram.

The control and arithmetic unit 11 then determines the position of the catheter 4 relative to the heart 3 from the data supplied and on the basis of the 3D image data sets present there can be derived an image of the anatomy surrounding the catheter in order to be displayed on a display device 13. Because this operation is continuously possible during the treatment, by observing the images displayed, in which each instantaneous position of the catheter or the catheter itself can be superposed, the attending physician can thus see where exactly the catheter is situated. He or she can thus very accurately address given points, for example within the heart, because according to the proposed method the eigenmotion of the heart is taken into account for determining the position of the catheter relative to the heart, and hence cannot lead to incorrect results.

Figure 2:
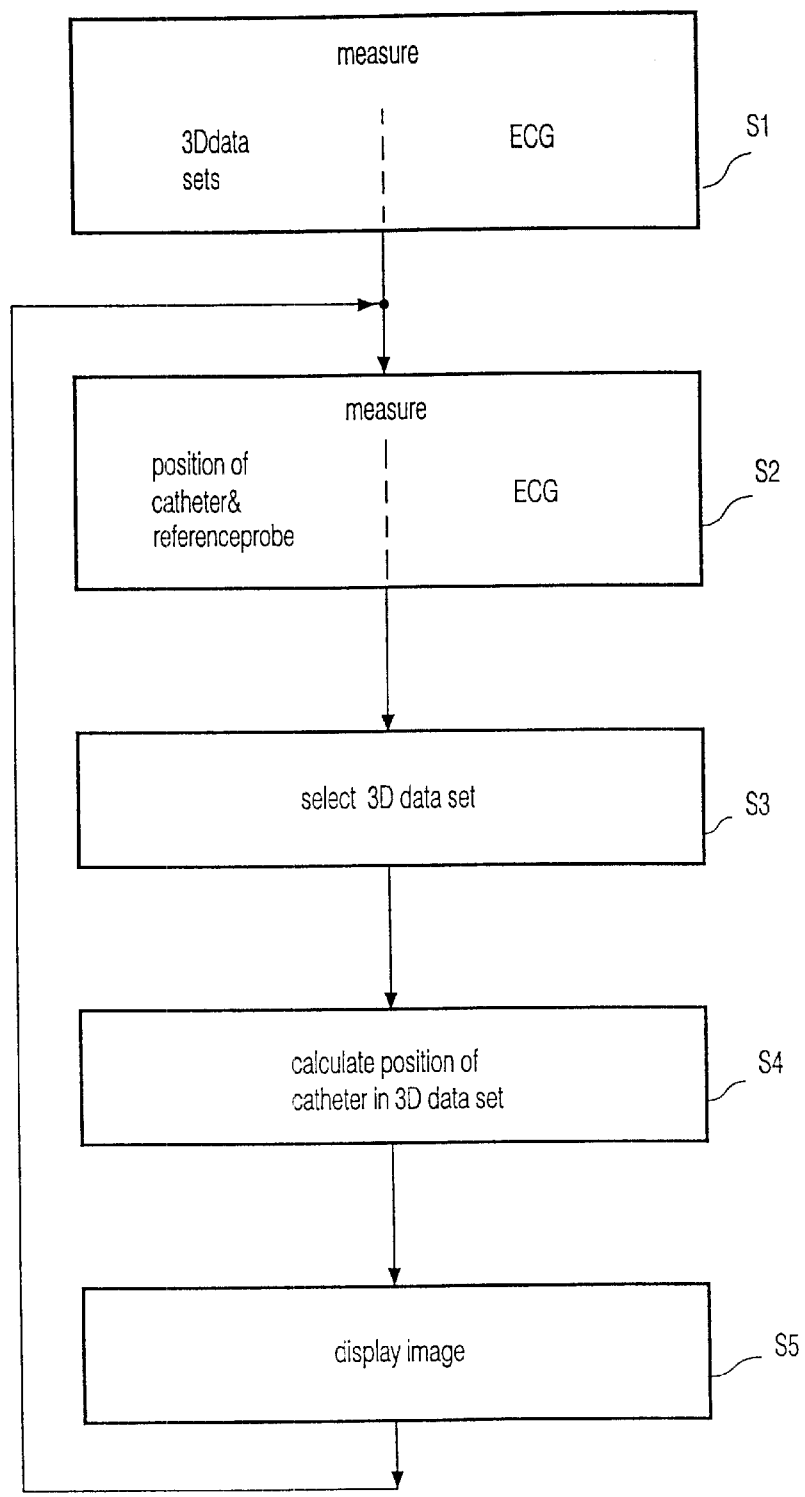
FIG. 2 shows a flow chart with the individual steps of the method.

The method according to the invention will be described in detail hereinafter with reference to the FIGS. 2 and 3. FIG. 2 shows the individual steps S1 to S5 of a flow chart. In the step S1, to be executed pre-operatively, the 3D image data sets are acquired, and at the same time also the electrocardiogram of the patient, so as to be stored as an image data base in the storage unit 12. During the subsequent steps of the method, to be executed during the treatment, the spatial positions of the catheter and of the reference probe are first measured by means of the position measuring unit in the step S2 while at the same time an electrocardiogram of the patient is recorded. On the basis of the motion phase of the heart, that is, on the basis of the instant within a period of the electrocardiogram at which this position measurement has taken place, that or those 3D image data sets which are associated with the same phase of motion, so with the same instant within the period of the electrocardiogram, are selected from the image data base in the step S3. Subsequently, in the step S4 the position of the catheter in the 3D image data set, and hence the position of the catheter relative to the heart for which image information is contained in the 3D image data set, is converted from the accurately measured spatial position of the catheter and of the reference probe, the selected 3D image data set and the information concerning the position of the reference probe relative to the 3D image data set. For this conversion the measured spatial position of the reference probe and the information concerning the position of the reference probe relative to the 3D image data set are used in such a manner that the position of the catheter relative to the reference probe is determined from the actually measured spatial positions of the catheter and the reference probe, after which it is taken up in the 3D image data set. Finally, an image of the heart on which the position of the catheter or the catheter itself is superposed can be determined from the selected 3D image data set.

The steps S2 to S5 can be carried out continuously during the treatment, thus enabling the physician to track the catheter with a high degree of reliability.

Figure 3:
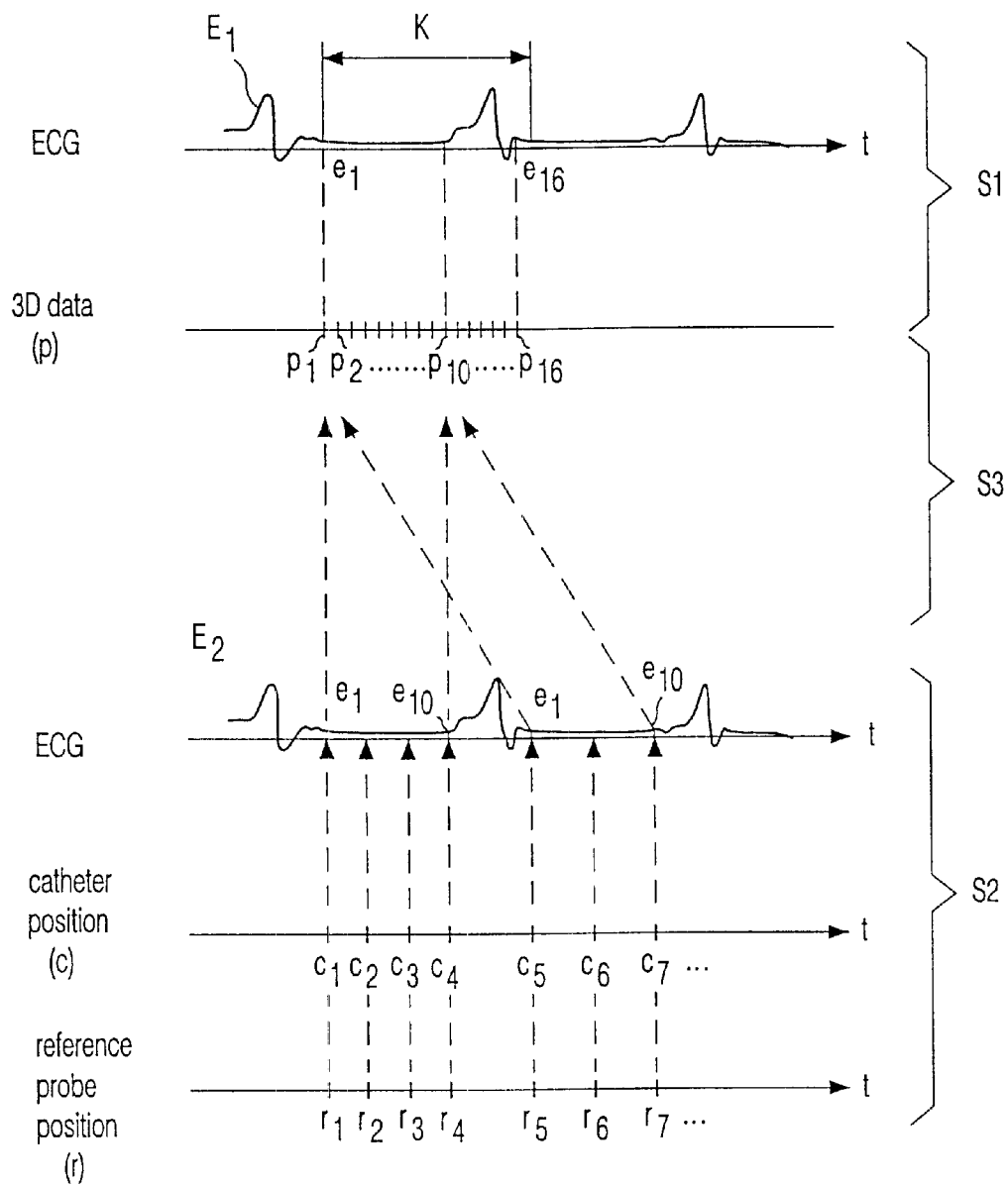
FIG. 3 shows several time diagrams illustrating individual steps of the method.

FIG. 3 shows several time diagrams in order to illustrate the steps S1 to S3. In the step SI to be carried out pre-operatively an electrocardiogram $E_1$ and 3D image data sets p are acquired at the same time. Acquisition is performed in such a manner that with each individual motion phase $e_1, e_2, \ldots, e_{16}$ within a period K of the electrocardiogram $E_1$ there is associated a respective 3D image data set $p_1, p_2, \ldots, p_{16}$. These pre-operatively acquired data sets are stored as an image data base. In the step S2, to be carried out during the treatment, an electrocardiogram $E_2$ is acquired again, the spatial positions c of the catheter and the spatial positions r of the reference probe being measured at the same time by means of the position measuring unit. This measurement of the catheter positions $c_1, c_2, \ldots, c_7$ and the reference probe positions $r_1, r_2, \ldots, r_7$ can be performed at the same or at different time intervals. Each position measurement, however, can again be associated with a given motion phase e within a period K of the electrocardiogram $E_2$ because of the simultaneous acquisition of the electrocardiogram $E_2$. For example, in the case shown the catheter positions $c_1$ and $c_5$ and the reference probe positions $r_1$ and $r_5$ have occurred in the motion phase $e_1$; the catheter positions $c_4$, $C_7$ and the reference positions $r_4$, $r_7$ have occurred in the motion phase $e_{10}$. On the basis of this motion phase that 3D image data set which is associated with the same motion phase is selected from the image data base in the step S3. In the present case this means that the 3D image data set $p_1$ is selected from the image data base on the basis of the motion phase $e_1$ and that on the basis of the motion phase $e_{10}$ the 3D image data set $p_{10}$ is selected. Thus, on the basis of the relevant motion phase a link is established between the actually measured catheter position and reference probe position and the 3D image data set acquired pre-operatively in the same motion phase.

Figure 4:
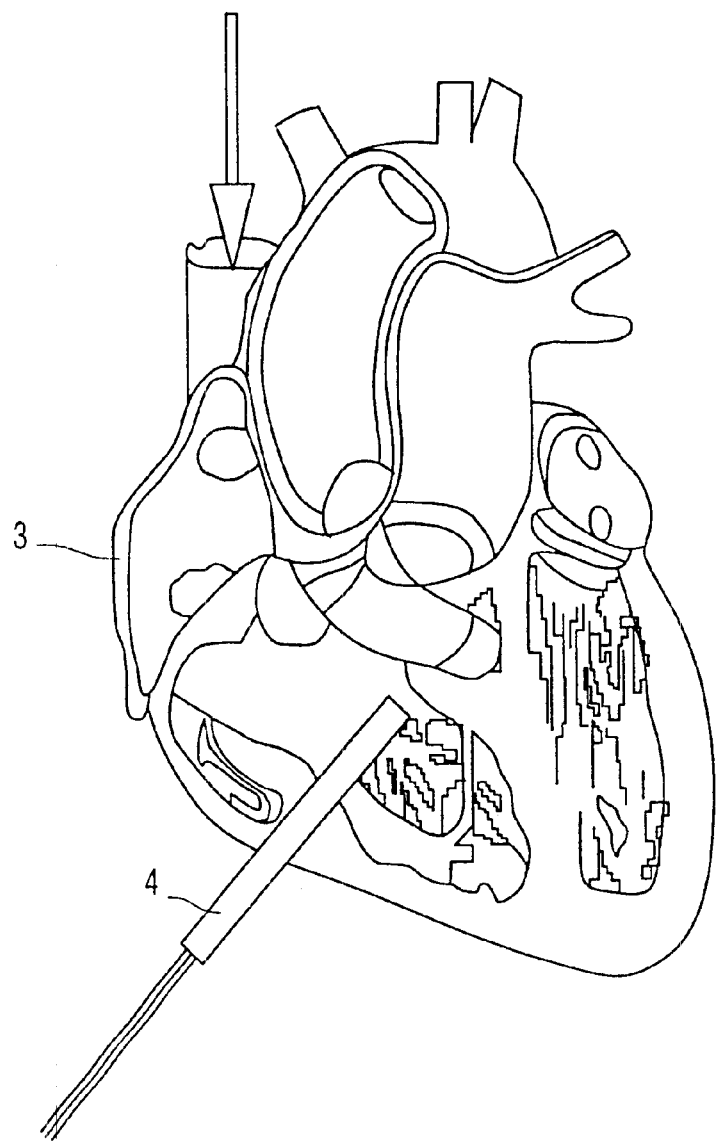
FIG. 4 is a representation of a human heart with a superposed catheter tip.

FIG. 4 shows an image of the heart 3 which has been acquired from a 3D data set and on which the catheter 4 is superposed.

Figure 5:
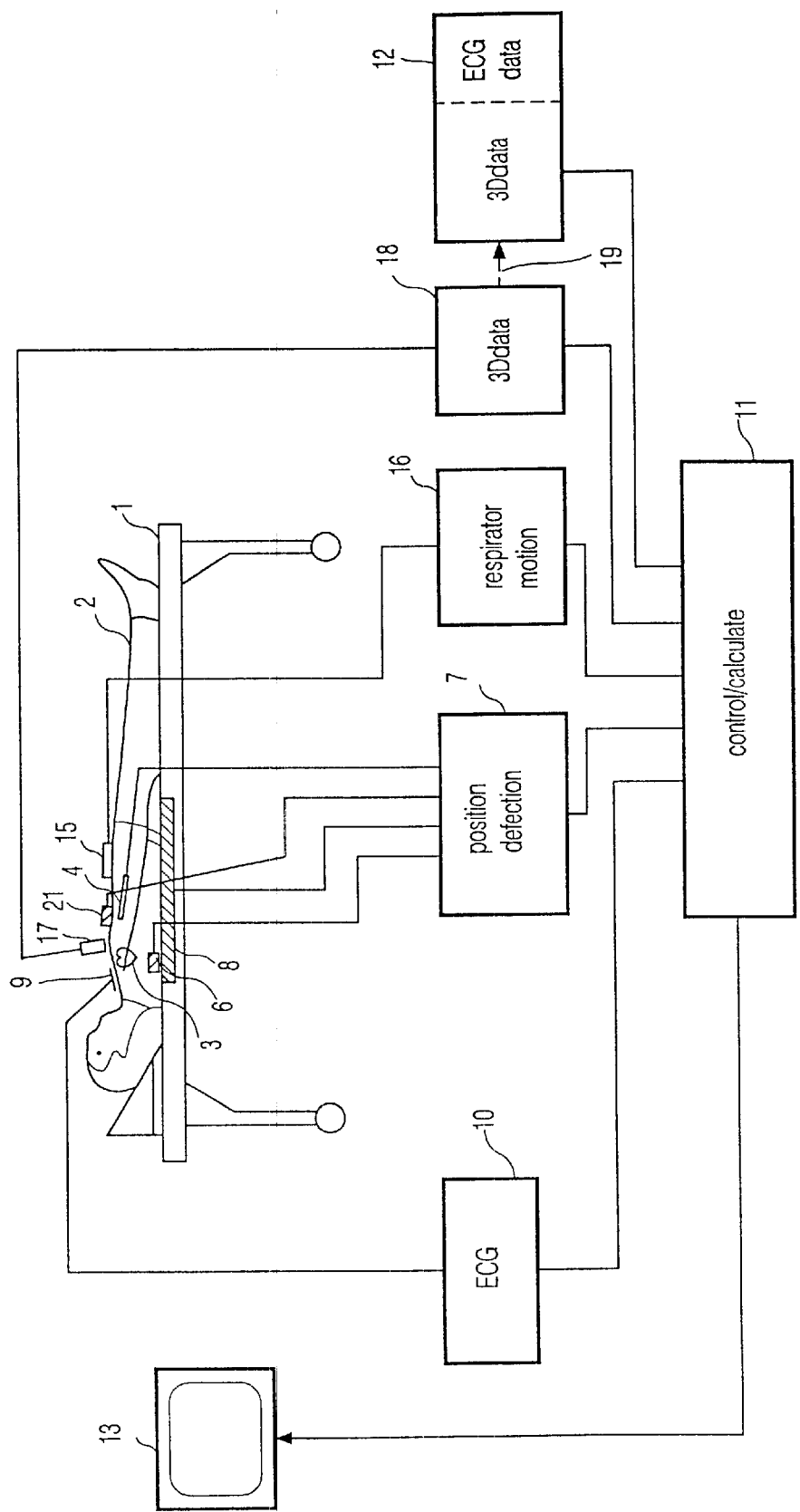
FIG. 5 shows a block diagram of a further embodiment of the invention.

FIG. 5 shows a block diagram of a further embodiment of the invention. In addition to the means shown in FIG. 1, this embodiment also includes a patient reference probe 21 which is arranged on the surface of the body of the patient 2. This probe is also connected to the RF processing unit 7 and its position in space is continuously measured, like the catheter position and the reference probe position. The measured position of the patient reference probe 21 can be advantageously used to take into account motions of the patient 2, during the treatment, for the determination of the position of the catheter relative to the heart. To this end, the relative position of the positions in space of the two reference probes 6, 21, the relative position in the initial state (state of rest of the patient) being known, is used to determine the extent of the change of position of the patient during the treatment and to correct it during the further calculation. The position in space of the catheter 4 relative to the patient reference probe 21 is subsequently used to convert the position in space of the catheter 4 relative to the 3D image data set and hence relative to the heart.

Moreover, this embodiment includes a respiratory motion sensor 15 which monitors the respiratory motion of the patient 2 and measures a respiratory motion signal which is applied to the respiratory motion measuring unit 16. The respiratory motion sensor may be, for example an elastically deformable abdominal belt which, as in the present case, is arranged at the area of the abdomen of the patient 2; other means are also feasible in this respect, for example an ultrasound device or a resistance measuring device which is arranged at the area of the abdomen of the patient in order to measure the electrical resistance of the patient 2 which varies because of the respiration. The respiratory motion signal which is continuously measured during the measurement of the positions in space of the catheter and the reference probes is also applied to the control and arithmetic unit 11 in which it is also taken into account in calculating the position of the catheter relative to the heart. This is advantageous because the catheter 4 is also moved within the body by the respiratory motion of the patient, so that the position of the catheter 4 relative to the reference probe 6 changes but the position of the catheter relative to the heart 3 does not change or only slightly so. If the respiratory motion phase were not taken into account during the measurement of the position in space of the catheter 4, the conversion of the position in space of the catheter 4 into a position relative to the heart 3 could possibly induce errors. The patient reference probe 21 may also suffice to perform the function of the respiratory motion sensor 15 and the respiratory motion measuring unit 16 in given circumstances, so that these elements could be dispensed with.

The embodiment shown in FIG. 5 also includes an ultrasound device 17 which is connected to an image data acquisition unit 18 and whereby actual; 3D image data sets can also be acquired in real-time during the treatment. Such actual 3D image data sets can then be associated, via a supply lead 19, with the individual motion phases and also be stored in the storage unit 12. It is also possible to apply such sets to the control and arithmetic unit 11 in which the actual 3D image data sets are also evaluated. This may offer an enhanced accuracy of the determination of the position of the catheter 4 and an enhanced image quality or more actual images of the anatomy surrounding the catheter, because the acquisition of the 3D image data sets stored in the image data base took place pre-operatively and the anatomy or its position could have changed slightly since then.

Figure 6:
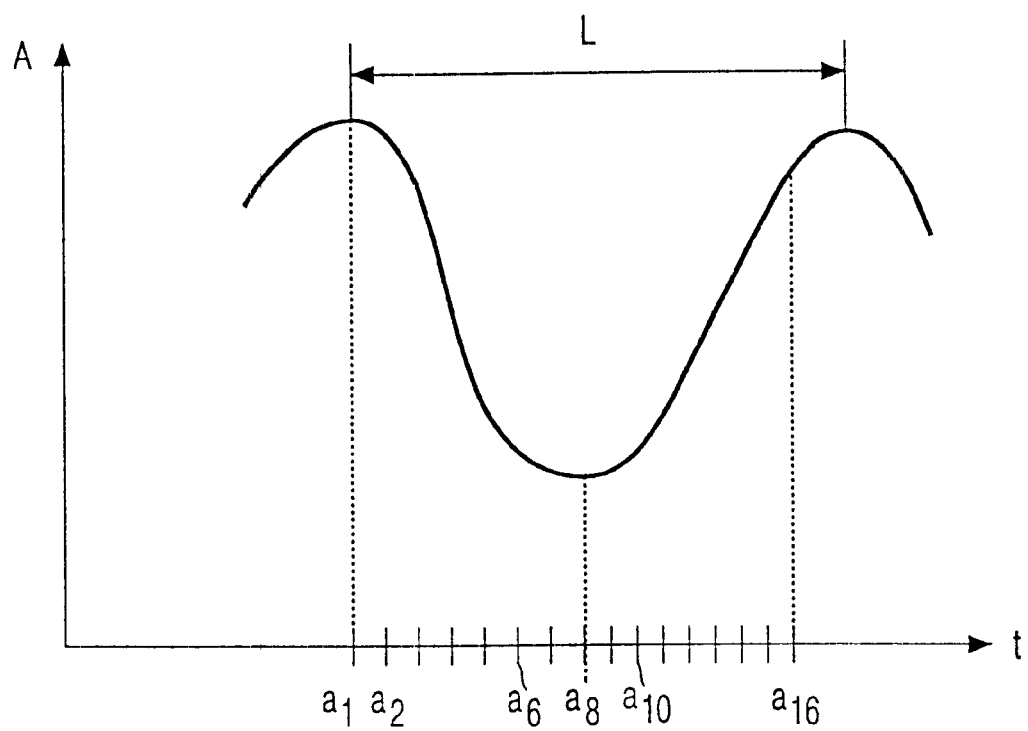
FIG. 6 shows a time diagram of a respiratory motion signal.

FIG. 6 shows a typical respiratory motion signal A which has been measured by means of a respiratory motion sensor 15 and is plotted on the time axis t. A respiratory motion signal essentially also varies periodically with the period L and can also be subdivided into individual respiratory motion phases $a_1, a_2, \ldots, a_{16}$.

As has been described with reference to FIG. 5, during the treatment this respiratory motion signal A can be continuously measured as a supplement to the electrocardiogram and be taken into account for calculating the position of the catheter relative to the heart. To this end, it is assumed that the position of the anatomy at the area of the heart changes by a fixed amount, in each respiratory motion phase a, relative to a given reference position relating to a given reference respiratory motion phase. These values can be acquired either on the basis of a model of the anatomy or be measured pre-operatively on the patient to be treated. Moreover, such a respiratory motion signal can already be acquired during the pre-operative acquisition of the 3D image data sets, so that the 3D image data sets are associated not only with the individual phases of motion of the electrocardiogram but also with individual phases of motion of the respiratory motion, so that a five-dimensional data set (3D image data set+cardiac motion phase+respiratory motion phase) is then stored in the image data base.

Alternatively, it may be arranged to acquire the 3D image data sets pre-operatively only during given, low-motion respiratory motion phases, for example during the respiratory motion phases $a_6$ to $a_{10}$, and to determine and evaluate also the spatial position of the catheter only during the same respiratory motion phases during the treatment.

Instead of the using of an electrocardiogram for the acquisition of the pre-operative 3D image data sets and for the intra-operative measurement of the spatial position of the catheter, another periodic signal which relates to a periodic motion of a body organ and causes a motion of the anatomy and/or the catheter in the treatment zone may also be used according to the method of the invention. For example, in the case of a treatment in the abdominal zone of the patient it is feasible to use the described respiratory motion signal (see FIG. 6) instead of an electrocardiogram.

The means for determining the various positions and signals as described with reference to the Figures are given merely by way of example. For example, the position measuring unit may have a different construction, for example, in that a receiving coil unit is provided on the catheter and on the reference probe whereas a transmission coil unit is arrange outside the patient. Instead of an electrocardiography unit for measuring an electrocardiogram, other means could be provided, for example, a pulse-oximetry device.

What is claimed is:

1. A method of determining the position of a medical instrument introduced into the body of a patient relative to a periodically moving organ of the body, which method includes the steps of:

a) determining the spatial position (c, r) of the medical instrument and of a reference probe including transmitting means which is arranged in a position outside the body of the patient while acquiring at the same time a periodic motion signal ($E_2$) which relates to the periodic motion of the body organ, b) selecting a 3D image data set (p) from an image data base which contains 3D image data sets (p) of the body organ which have been acquired pre-operatively and simultaneously with the same motion signal ($E_1$) and are associated with individual motion phases ($e_1, e_2, \ldots$), in such a manner that that 3D image data set (p) is selected which is associated with the motion phase ($e_1, e_2, \ldots$) during the determination of the spatial position (c, r) of the medical instrument and of the reference probe, and c) determining the position of the medical instrument relative to the body organ by converting the spatial position (C) of the medical instrument by means of the positions of the reference probe which are known in space and in the selected 3D image data set.

2. A method as claimed in claim 1, wherein an electrocardiogram ($E_1, E_2$) and/or a respiratory motion signal (A) which is dependent on the respiratory motion of the patient is acquired as the motion signal.

3. A method as claimed in claim 1, wherein the image data base contains 3D image data sets (p) which have been acquired by means of an image data acquisition unit which may comprise a magnetic resonance device, an X-ray device, a computed tomography device and/or an ultrasound device.

4. A method as claimed in claim 1, wherein a 3D image data set is also acquired during the determination of the spatial position (r) of the medical instrument and of the reference probe using ultrasound means which image data set is used to determine the position of the medical instrument relative to the body organ and/or is taken up in the image data base.

5. A method as claimed in claim 1, wherein simultaneously with the determination of the spatial position (c, r) of the medical instrument and of the reference probe there is measured a respiratory motion signal (A) which represents the respiratory motion of the patient and is used for correction purposes during the determination of the position of the medical instrument relative to the body organ.

6. A method as claimed in claim 5, wherein the correction is performed in such a manner that the correction value associated with the actually measured respiratory motion phase is selected from a pre-operatively determined correction table which contains correction values for the correction of the effect of the respiratory motion on the position of the body organ to be examined, in dependence on the individual respiratory motion phases, the position (c) in space of the medical instrument being corrected on the basis thereof.

7. A method as claimed in claim 1, wherein an image of the vicinity of the medical instrument is determined from the selected 3D image data set (p) so as to be displayed on a display device, the position of the medical instrument being superposed on said image.

8. A method as claimed in claim 1, wherein the position of the reference probe relative to a 3D image data set is determined in that the reference probe is also reproduced upon acquisition of the 3D image data sets (p) or in that the position of the reference probe is determined relative to an image data acquisition unit acquiring the image data sets (p).

9. A method as claimed in claim 1, wherein the reference probe is arranged so as to be fixed in space, that the spatial position of a patient reference probe arranged on the patient is determined during the step a), and that during the step c)

the known position in space of the patient reference probe is used for the determination of the position of the medical instrument relative to the body organ in order to take into account motions of the patient.

10. A device for determining the position of a medical instrument, introduced into the body of a patient, relative to a periodically moving body organ, which device includes:

- a position measuring unit for determining the spatial position (c, r) of a medical instrument introduced into the body and of a reference probe including transmitting means arranged outside the body,
- a signal measuring unit for determining a periodic motion signal ($E_2$) r related to the periodic motion of the body organ, simultaneously with the determination of the spatial position (c, r) of the medical instrument and of the reference probe,
- a storage unit for storing an image data base containing 3D image data sets (p) of the body organ which have been acquired pre-operatively and simultaneously with the same motion signal ($E_1$) and are associated with individual motion phases ($e_1, e_2, \ldots$), and
- a control and arithmetic unit for selecting a 3D image data set (p) from the image data base in such a manner that that 3D image data set (p) is selected which is associated with the motion phase ($e_1, e_2$) during the determination of the spatial position (c, r) of the medical instrument and of the reference probe, and for determining the position of the medical instrument relative to the body organ by converting the spatial position (c) of the medical instrument by means of the positions of the reference probe which are known in space and in the selected 3D image data set.

11. A device as claimed in claim 10, wherein a signal measuring unit includes an electrocardiography unit for measuring an electrocardiogram ($E_2$) of the patient.

12. A device as claimed in claim 10, wherein the signal measuring unit includes means for measuring the respiratory motion of the patient simultaneously with the determination of the spatial position (c, r) of the medical instrument and of the reference probe.

13. A device as claimed in claim 10, wherein the position measuring unit includes electromagnetic transmission means which are arranged outside the body of the patient, or on the medical instrument and the reference probe, as well as corresponding electromagnetic receiving means which are arranged on the medical instrument and the reference probe or outside the body of the patient, respectively.

14. A device as claimed in claim 10, wherein the reference probe is arranged so as to be stationary in space and that there is provided a patient reference probe which is attached to the patient.

* * * * *